US012770723B2

(12) United States Patent
Al Anouti et al.

(10) Patent No.: US 12,770,723 B2
(45) Date of Patent: Oct. 20, 2026

(54) VITAMIN D DEFICIENCY DIGITAL MONITORING SYSTEM

(71) Applicant: Zayed University, Dubai (AE)

(72) Inventors: Fatme Mohamad Al Anouti, Abu Dhabi (AE); Reem Salem Mohammed Salem, Ontario (CA); Justin Olutunde Thomas, Abu Dhabi (AE)

(73) Assignee: Zayed University, Dubai (AE)

( * ) Notice: Subject to any disclaimer, the term of this patent is extended or adjusted under 35 U.S.C. 154(b) by 0 days.

(21) Appl. No.: 18/977,769

(22) Filed: Dec. 11, 2024

(65) Prior Publication Data

US 2026/0162796 A1 Jun. 11, 2026

(51) Int. Cl.

| | |
|---|---|
| ***G16H 20/10*** | (2018.01) |
| ***A61B 5/00*** | (2006.01) |
| ***G01J 1/44*** | (2006.01) |
| ***G16H 10/60*** | (2018.01) |
| *G01J 1/42* | (2006.01) |

(52) U.S. Cl.

CPC ............. *G16H 20/10* (2018.01); *A61B 5/441* (2013.01); *G01J 1/44* (2013.01); *G16H 10/60* (2018.01); *G01J 2001/4266* (2013.01)

(58) Field of Classification Search

None

See application file for complete search history.

(56) References Cited

U.S. PATENT DOCUMENTS

| | | | | |
|---|---|---|---|---|
| 2014/0019151 | A1* | 1/2014 | Adami | G16H 50/20 705/2 |
| 2019/0099613 | A1* | 4/2019 | Estes | A61N 5/0616 |
| 2020/0376292 | A1* | 12/2020 | Moffat | G16H 20/13 |

OTHER PUBLICATIONS

Hyppönen et al. ("Adiposity, vitamin D requirements, and clinical implications for obesity-related metabolic abnormalities," Nutrition Reviews, vol. 76, Issue 9, Sep. 2018, pp. 678-692) (Year: 2018).*

* cited by examiner

*Primary Examiner* — Christopher B Tokarczyk

(57) ABSTRACT

A method includes receiving vitamin D electronic information. The computing device has a light sensor, an ultraviolet sensor, and a display screen. The method includes determining a particular amount of International Units (IU) needed for a particular amount of vitamin D dosage. The particular amount of IU needed for the particular amount of vitamin D dosage is a product of UV index, skin type factor, body exposure, age factor, and 1000. The determining the particular amount of IU needed for the particular amount of vitamin D dosage is conducted in real-time. The method includes sending, by the computing device, the particular amount of IU needed for the particular amount of vitamin D dosage to a display screen.

10 Claims, 15 Drawing Sheets

300

600

700

800

1200

1300

VITAMIN D DEFICIENCY DIGITAL MONITORING SYSTEM

BACKGROUND

Hypovitaminosis D is a significant health concern in the United Arab Emirates (UAE), particularly among females. Wearable devices designed to encourage safe sun exposure could potentially help individuals achieve and sustain healthy vitamin D levels.

Vitamin D is essential for regulating the metabolism of bone minerals, including calcium and phosphorus. Sunlight is the primary source of vitamin D, supplying 90% of the body's needs, with the rest deriving from diet and other sources. Upon exposure to ultraviolet B radiation, the sun stimulates vitamin D synthesis in the skin, providing the body with its primary internal source of this vitamin.

Studies show that vitamin D deficiency negatively impacts individuals'health and well-being, including bone issues, cardiovascular diseases, diabetes, autoimmune diseases, cancer, and anxiety disorders. Furthermore, due to its negative consequences on the health of the mother and fetus during pregnancy and nursing, vitamin D deficiency can become a critical concern. While there are significant issues that result from vitamin D deficiency, there is currently no practical way to measure vitamin D levels on a continuous and real-time basis.

DETAILED DESCRIPTION OF PREFERRED EMBODIMENTS

Figure 1A:
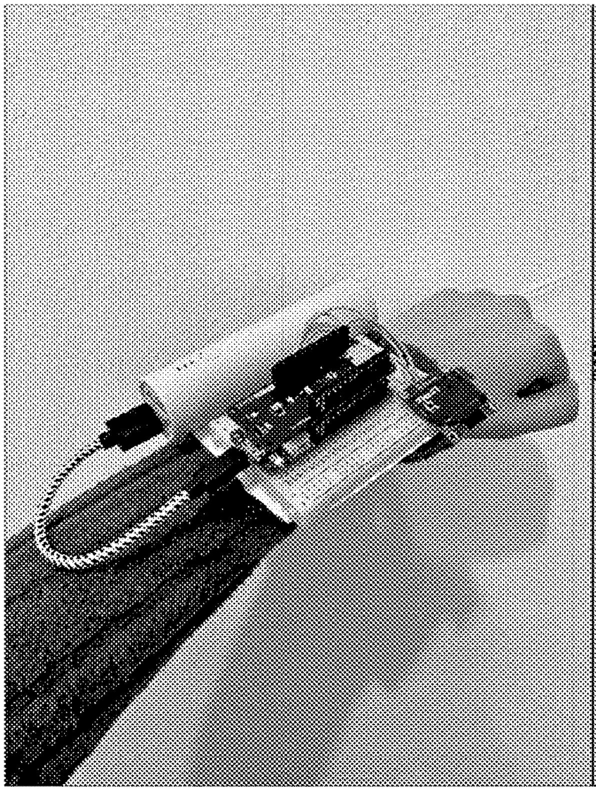
FIGS. 1A and 1B are diagrams of an example apparatus.

The following detailed description refers to the accompanying drawings. The same reference numbers in different drawings may identify the same or similar elements.

Systems, devices, and/or methods described herein are for heliometric device, a wearable technology designed to quantify, monitor, and encourage safe sun exposure, emerges as an encouraging step toward addressing widespread vitamin D deficiency. This device provides accurate and real-time data about a person's sun exposure through the integration of the Internet of Things (IoT) technology, supporting informed decisions for healthy sun exposure practices. The heliometric device is an example of digital technology in service of public health, specifically addressing the issue of improving vitamin D levels.

In embodiments, an example heliometric device to evaluate its perceived usability, wearability, and effectiveness. Furthermore, the example apparatus is analyzed for safe and healthy sun exposure practices, acting as a countermeasure to the prevalent challenge of hypovitaminosis D. In embodiments, the heliometric device data is encrypted and stored in a cloud environment. In embodiments, the encryption may utilize AES-256 algorithm, using secure data transmission protocols (TLS), including two-step verification, and limiting access to participants'data to only one researcher responsible for the device development.

In a non-limiting example, participants may wear the example heliometric device daily under direct sunlight for 10 minutes over one week. For example, sun exposure periods were fixed for participants to ensure a unified experience. In embodiments, the 10-minute sun exposure recommendation aligns with prior research advocating for 10-15 minutes of direct sunlight at least thrice weekly, without the use of sunscreen.

In this non-limiting example, participants were advised to divide the daily 10 minute into two sessions: 5 minutes straight between 9:00 a.m. and 12:00 p.m., and another 5 minutes straight between 3:00 p.m. and 4:00 p.m., while avoiding the sun between 12:00 p.m. and 3:00 p.m. to prevent any potentially harmful effects. Participants were provided instructions to stop wearing sunscreen while actively using the device along with keeping the device away from water due to its sensitive parts.

In this non-limiting example, users enable their smartphone's Personal Hotspot or a standalone portable Wi-Fi Hotspot in order to connect their device to the internet. Hotspot's Wi-Fi names and passwords were programmed into each participant's personal device. Additionally, detailed instructions were provided on how to wear the device, wrap it around their wrist, view details on the display, turn it on and off, connect it to the personal hotspot, and charge it.

In embodiments, participants download a monitoring application onto their own user device (e.g., smartphone). Using the monitoring application, a user can enter personal information, such as their age, weight, height, body exposure percentage, and skin type. In the monitoring application, the user can use an electronic dashboard to view their daily sun exposure and other personal information. In embodiments, each user of the monitoring application is provided with a unique number to not only recognize their personal dashboard but also to add a layer of security and anonymity.

Figure 1B:
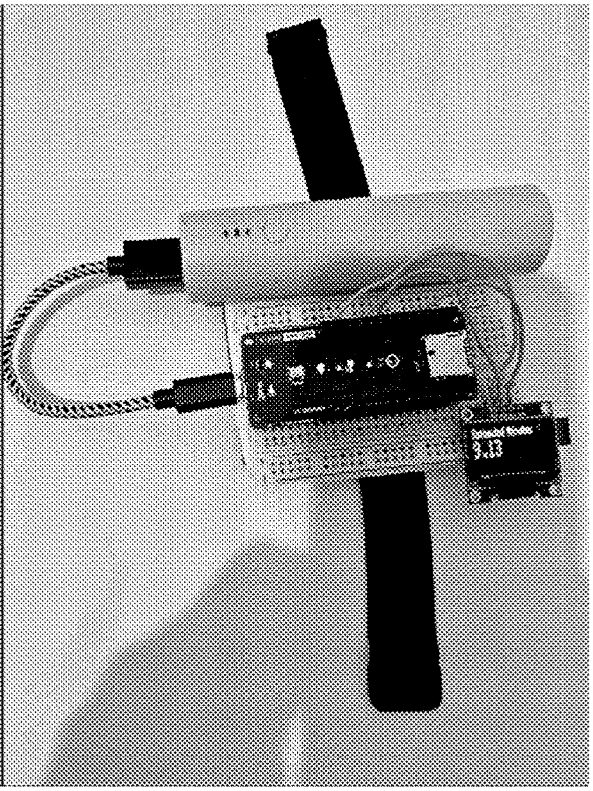

FIGS. 1A and 1B describe a heliometric device. In embodiments, the heliometric device monitors and recommends safe sun exposure. In embodiments, the heliometric device can have a wrist strap, similar to a smartwatch. In embodiments, the heliometric device includes a microcontroller board (e.g., such as, but not limited to Arduino MKR1000). In embodiments, the heliometric device includes a shield (e.g., such as, but not limited to, Arduino MKR ENV Shield) mounted on top of the microcontroller. In embodiments, the shield has several sensors, such as a light sensor (e.g., TEMT6000 or any other type of light sensor) and an ultraviolet (UV) sensor (e.g., VEML6075 or another type of ultraviolet sensor), and/or other types of sensors. In embodiments, the light sensor determines sun exposure and the UV sensor is used to receive information about ultraviolet. In embodiments, the heliometric device has a display screen that shows sun exposure information, such as the total minutes needed to be under the sun (for example, 10 minutes), cumulative minutes spent under the sun, and the percentage of the estimated vitamin D intake based on sun exposure data. In embodiments, the heliometric device has a power system (e.g., power bank, batteries, etc.).

In embodiments, the heliometric device can use Internet of Things (IoT) technologies. In embodiments, the heliometric device can be connected to a database (e.g., cloud database), which updates participants'sun exposure data and stores this information in a database. In embodiments, a monitoring application may be used on a user device and obtains and sends electronic information on sun exposure to/from the heliometric device. In embodiments, the heliometric device sends data to and receives data from another computing device (e.g., via a network or from a cloud computing system). In embodiments, the monitoring application, through mobile phones, can access the same data by connecting to the Arduino Cloud. The monitoring application can also send data to the Arduino Cloud, which then it will be stored. Accordingly, the heliometruc device does not directly communicate with other devices, like mobile phones, over Bluetooth or WiFi. Instead, it relies on the Arduino Cloud as an intermediary.

In embodiments, users enter information into the monitoring application such as their weight, height, age, skin color, and body exposure %. In embodiments, users can view their daily sun exposure progress on both the mobile app and display screen on the heliometric device.

In embodiments, the heliometric device can be used at different times of the day and also in different geographic locations. In embodiments, the heliometric device can receive LUX measurement under different conditions (e.g., outdoors under direct sunlight, outdoors under shade, and indoors). In embodiments, the heliometric device may have a sensor that has a threshold of 650 LUX, where any number above that would be considered sun exposure, and any number equal to or less than that would be considered non-exposure.

In embodiments, the heliometric device and/or monitoring application may store a variable that includes a timestamp when the illuminance amount exceeds a certain threshold, indicating the person is under sunlight. In embodiments, the heliometric device and/or the monitoring application may also include a variable that stores the timestamp when the illuminance amount drops below that threshold, indicating the person is no longer under sunlight. In embodiments, the heliometric device and/or monitoring application may include a variable that records the time spent under the sun during each period of exposure.

Figure 2:
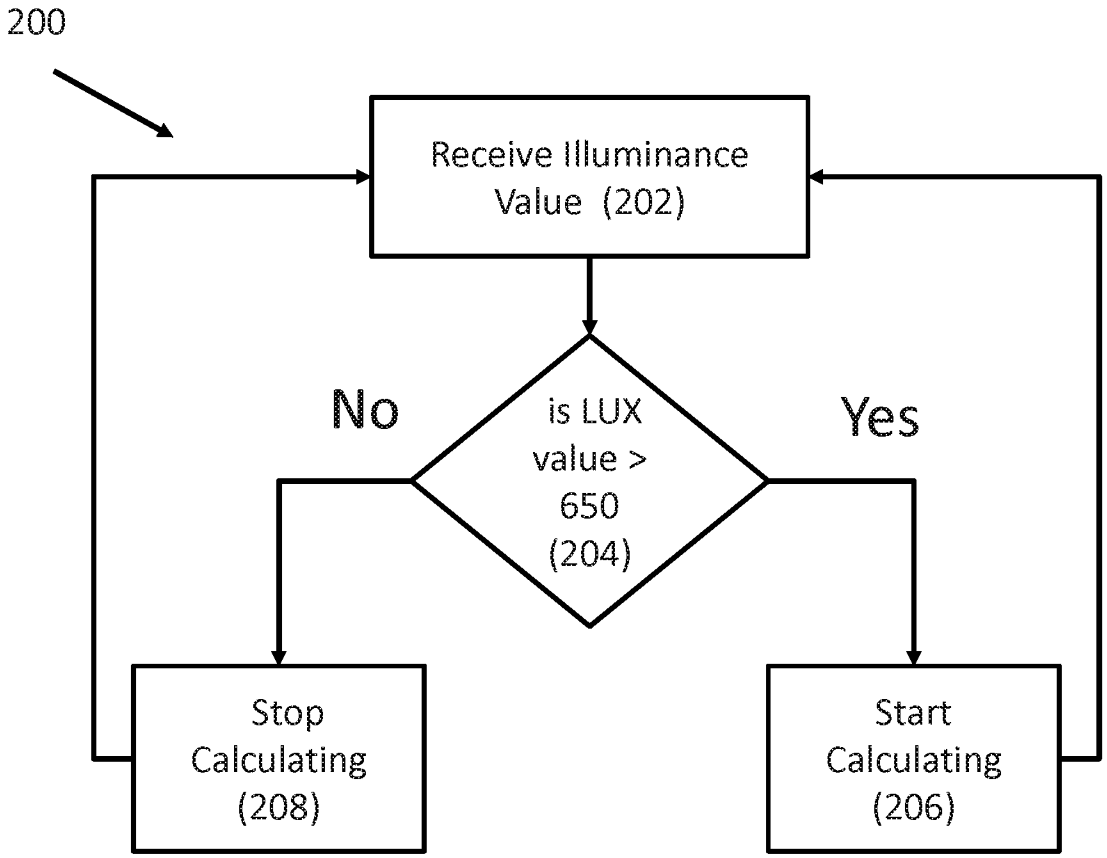
FIG. 2 is a diagram of an example flowchart.

FIG. 2 describes flowchart 200. In embodiments, flowchart 200 may be performed by a heliometric device. At step 202, the heliometric device receives illuminance information (e.g., LUX information via a sensor on the heliometric device). At step 204, heliometric device determines if the LUX value is greater or equal to 650 LUX, or less than 650 LUX. Accordingly, the light sensor of heliometric device continuously measures light levels, and based on the readings, accumulate sun exposure minutes only when the sun exposure threshold is met. Furthermore, a timestamp of when the light is detected based on the number of milliseconds.

If light sensor detects a LUX level above 650 (step 204—YES), the device interprets this as the wearer being in direct sunlight, and it starts counting this time towards the daily sun exposure goal (i.e., starts calculating vitamin D exposure in step 206). However, if the light sensor detects a LUX level below or equal to 650 (step 204—NO), the heliometric device determines that the person is not in an environment with adequate sunlight for vitamin D synthesis, and thus not counted toward sun exposure (i.e., stops calculating vitamin D exposure in step 208). At both steps 206 and 208, the heliometric device continues to receive additional sunlight exposure and again goes through step 204 to determine if the LUX reading is greater or equal, or less than 650. In embodiments, the heliometric device sends real-time light sensor readings every 4 seconds to a database where the information is stored. This occurs at step 206 and also at step 208.

In embodiments, the heliometric device determines the duration of being under the sun for the user by subtracting the timestamp when the light level fell below the threshold (650 LUX) from when it exceeded the threshold (greater than 650). Thus, this calculation gives the duration in milliseconds that the light sensor detected illuminance above 650 lux. In embodiments, the heliometric device also determines the total amount of time that a person has been exposed to sunlight.

In embodiments, the heliometric device determines if a person transitions immediately from sunlight to darkness. In addition, the heliometric device determines if a person has been under sunlight for 10 seconds or more. If the amount of time under sunlight is greater than a specific duration (in this case, 10 seconds), the heliometric device adds that time to other time durations whenever the person is under sunlight.

In embodiments, the sunlight exposure electronic information is analyzed using quantitative methods (mean, median, standard deviation, etc.). In embodiments, thematic analysis is a method for identifying, examining, and interpreting patterns or themes within data. Accordingly, this provides a comprehensive understanding of participants'experiences with the heliometric device.

In embodiments, the formula for calculating the estimated IU (International Units) needed for vitamin D dosage IU/day=UV index*skin type factor*body exposure*age factor*1000 (the standard IU). For example, if the UV index=10, then the value used in the above formula is 1; and if the UV index is 4, then the value in the above formula is 0.4. For example, skin factor 2 has a value of 1 for the above formula, skin factor 3 has a value of 0.8 for the above formula, skin factor 4 has a value of 0.6 for the above formula, and skin factor 5 has a value of 0.4 for the above formula. For body exposure, if fully exposed, a value of 100% is used; for face, neck, back of hands, and arms, a value of 22% is used; and for face and back of hands, a value of 8% is used. For age factor, if the age is 0 to 22, then the age factor is 1; if the age is 23 to 40, the age factor is 0.83; if the age is 41 to 59, the age factor is 0.66; and, if the age is 60 or above, the age factor is 0.49. If the user's body mass index (BMI) is above 30, then the above formula includes a factor of 0.7. In addition, the estimated minutes under the sun is determined by 1000/IU, where IU is from the formula described in this paragraph.

In a non-limiting example, participants are nine female students recruited from a university in Abu Dhabi, UAE. All participants exhibited hypovitaminosis D with no active vitamin D supplementation, averaging a vitamin D serum level of 41.6 nmol/L (16.64 ng/mL). Participants were aged 19-21 years and had an average Body Mass Index (BMI) of 22 (kg/m2) and a skin type of 3-4 on the Fitzpatrick scale. In this non-limiting example, participants wear the device for 10 minutes daily over the course of one week. Additionally, heliometric device usage from the heliometric device data which includes sun exposure times recorded by its light sensors. Compared to participants'feedback, data from the heliometric device reveals that participants used the heliometric device for an average of 6 days out of 7 and were exposed to the sun for an average of 8.5 min daily.

In this non-limiting example, some issues prevent the heliometric device from calculating sun exposure time, such as cloudy days (n=5, n being the number of participants) and connection challenges with smartphones (n=2). In this non-limiting example, the majority of participants (n=8) used the device in their house yard or garden, whereas only one participant used it while traveling to Sharjah (a neighboring Emirate) or on her house's balcony. Afternoon sessions were favored by several participants (n=4) compared to morning ones (n=1), while four participants mixed between morning, noon, and afternoon sessions. Seven participants preferred being under the sun for 10 min consecutively, while two either divided the period into 5 min each or opted for a mix between the different styles.

Figure 3:
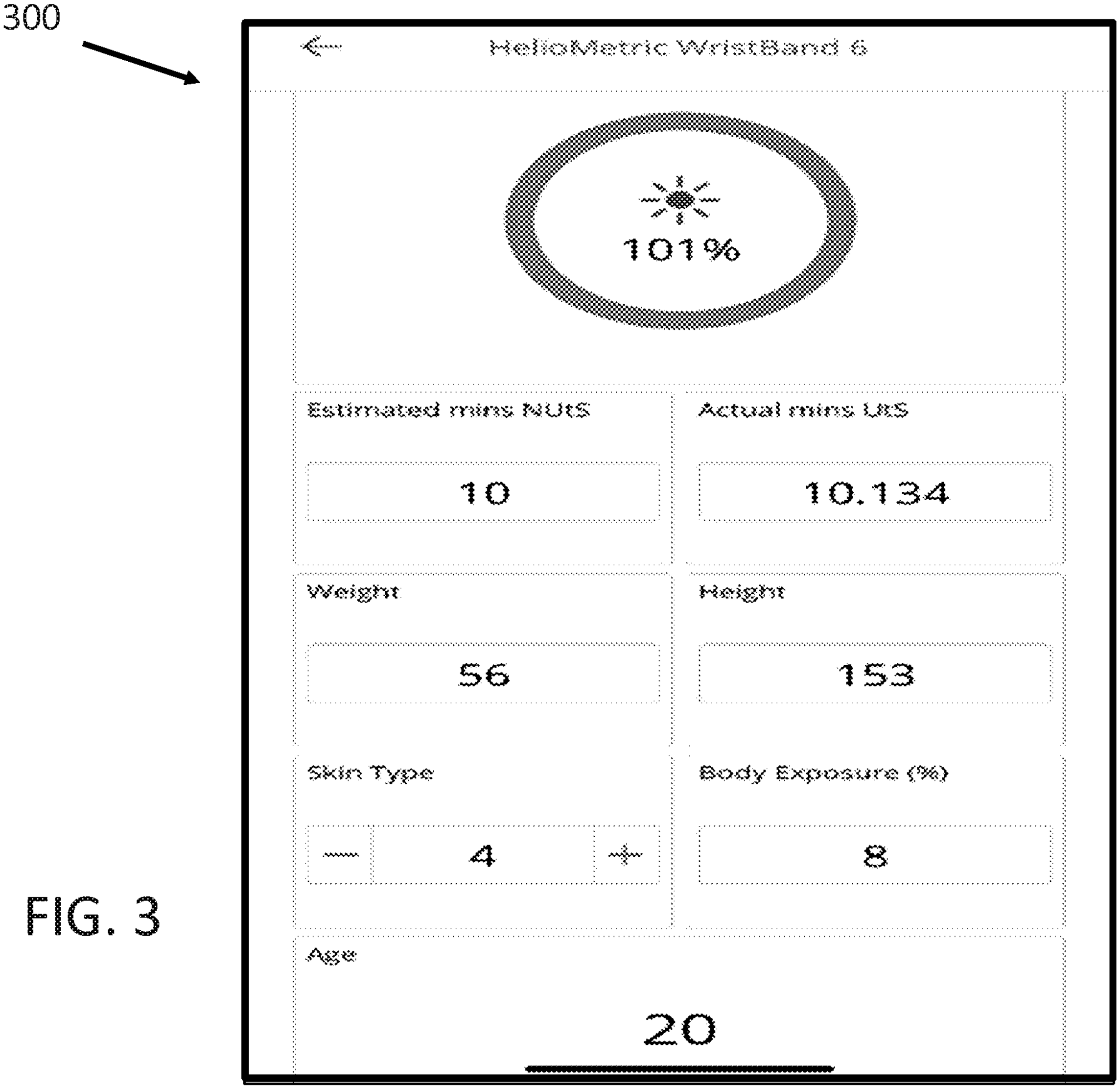
FIG. 3-13 are diagrams of example screenshots.

FIGS. 3 to 13 describe different electronic screenshots that may be displayed on a user device or on a heliometric device. FIG. 3 shows example screenshot 300. As shown in FIG. 3, screenshot 300 includes information about the user of the heliometric device (such as weight, height, and skin type). Also, as shown in FIG. 3, screenshot 300 includes the Estimated minutes Needed Under the Sun (NUtS) and the Actual minutes Under the Sun (UtS). In embodiments, The Estimated minutes Needed Under the Sun (NUtS) and the Actual minutes Under the Sun (UtS). In embodiments, estimated mins needed under the sun is related to the estimated minutes needed under the sun that was calculated by our formula. These minutes might be different from one person to another based on the age, skin type, weight, height, etc. In embodiments, actual mins is actual mins under the sun which is related to the actual minutes that the person spent under the sun. This is calculated using the light sensor as discussed above.

Figure 4:
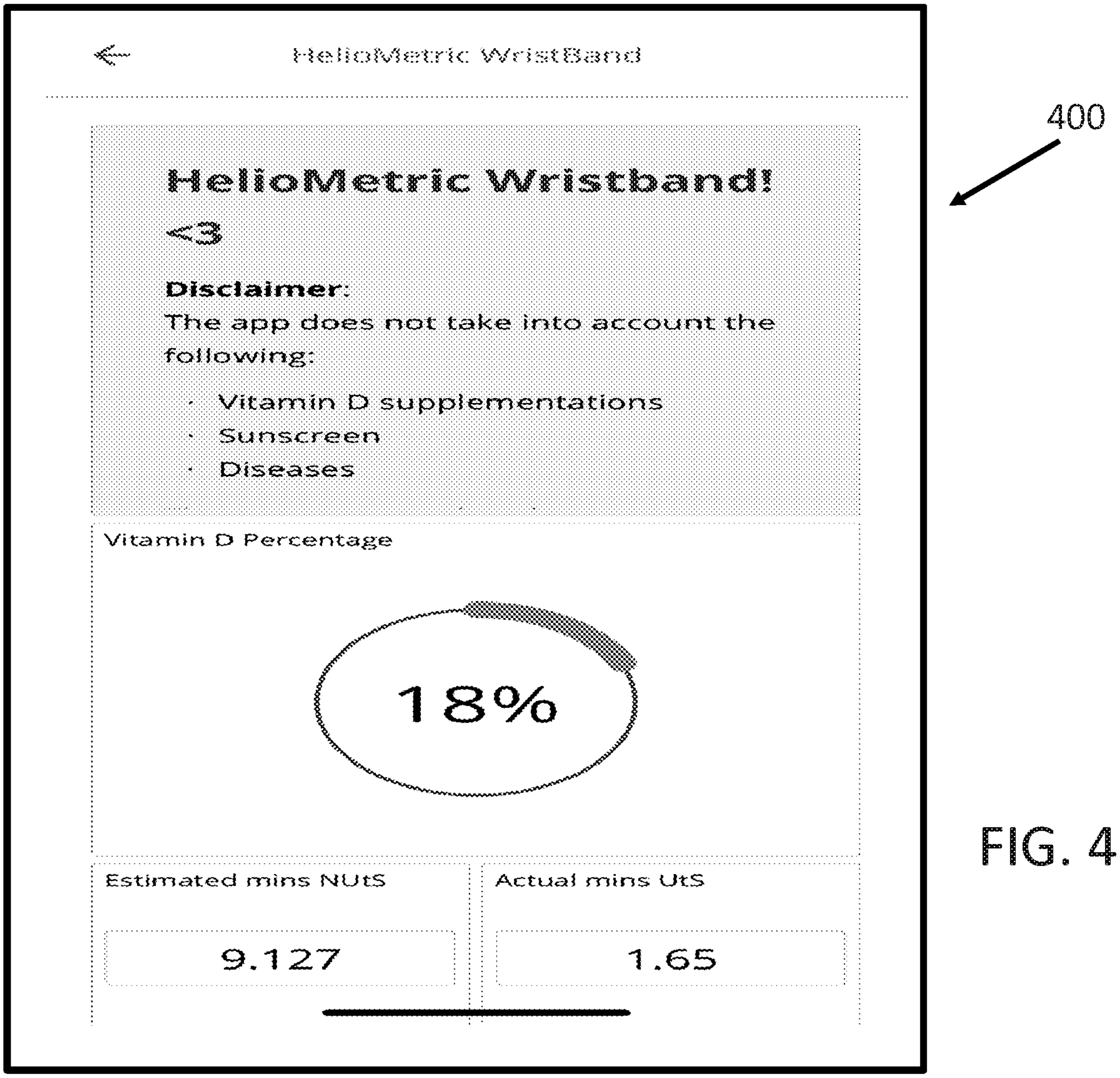
Figure 5:
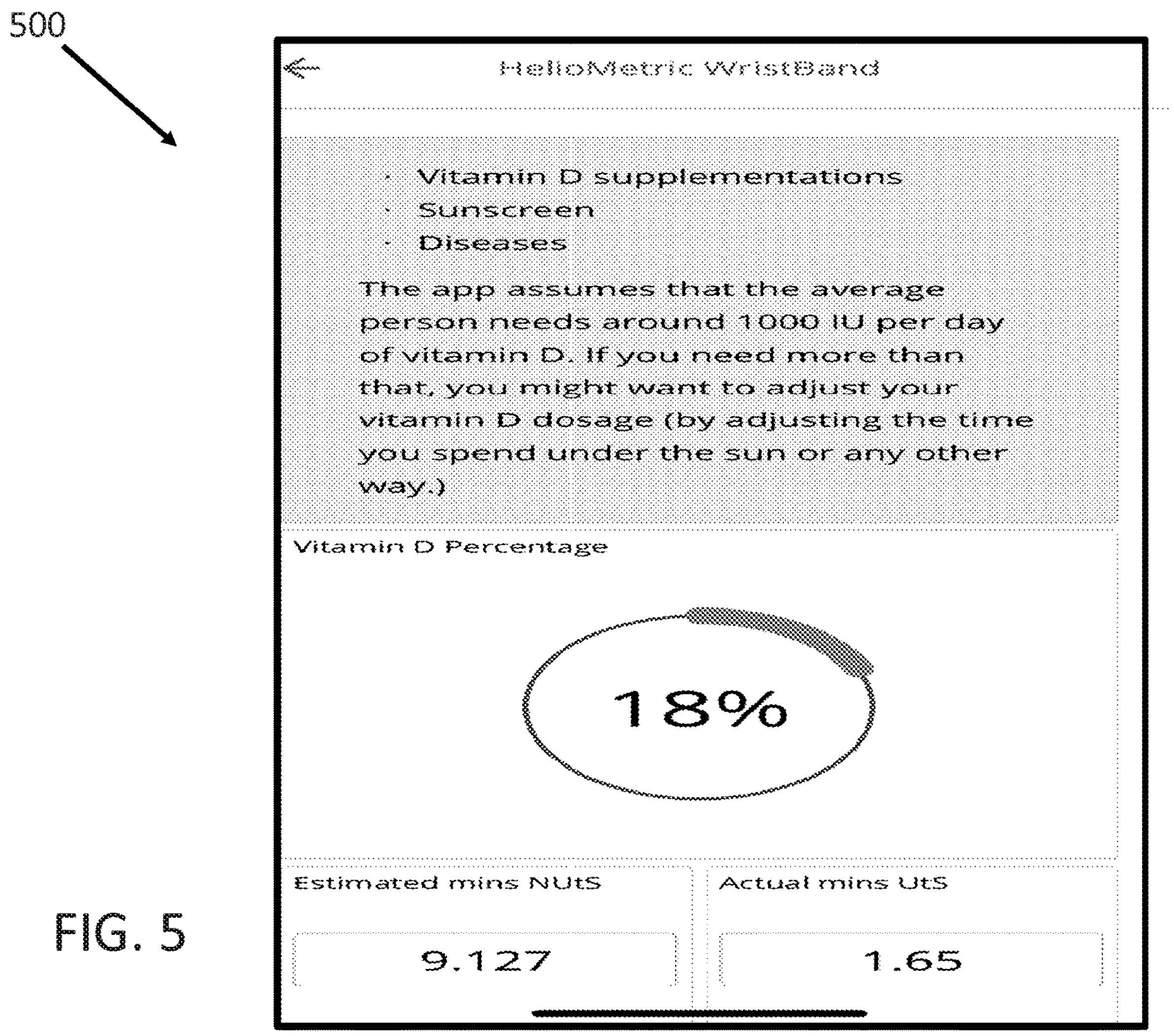
Figure 6:
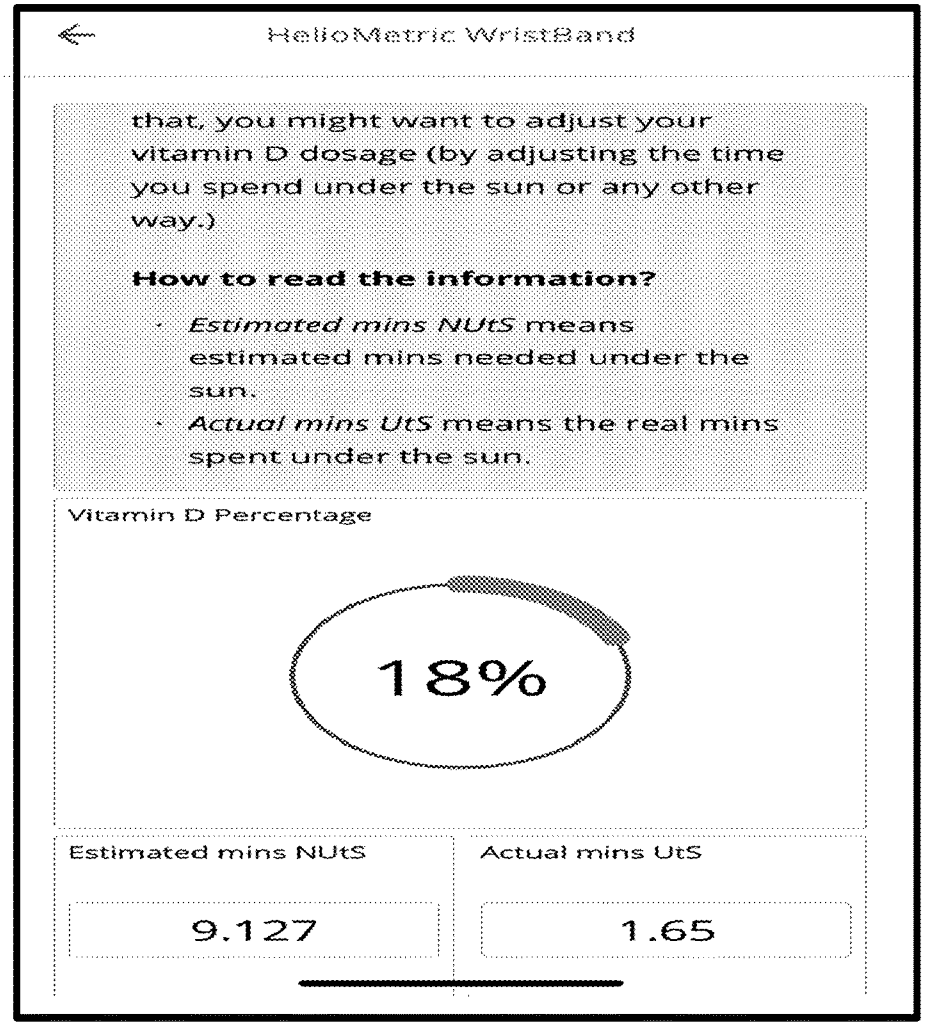
Figure 7:
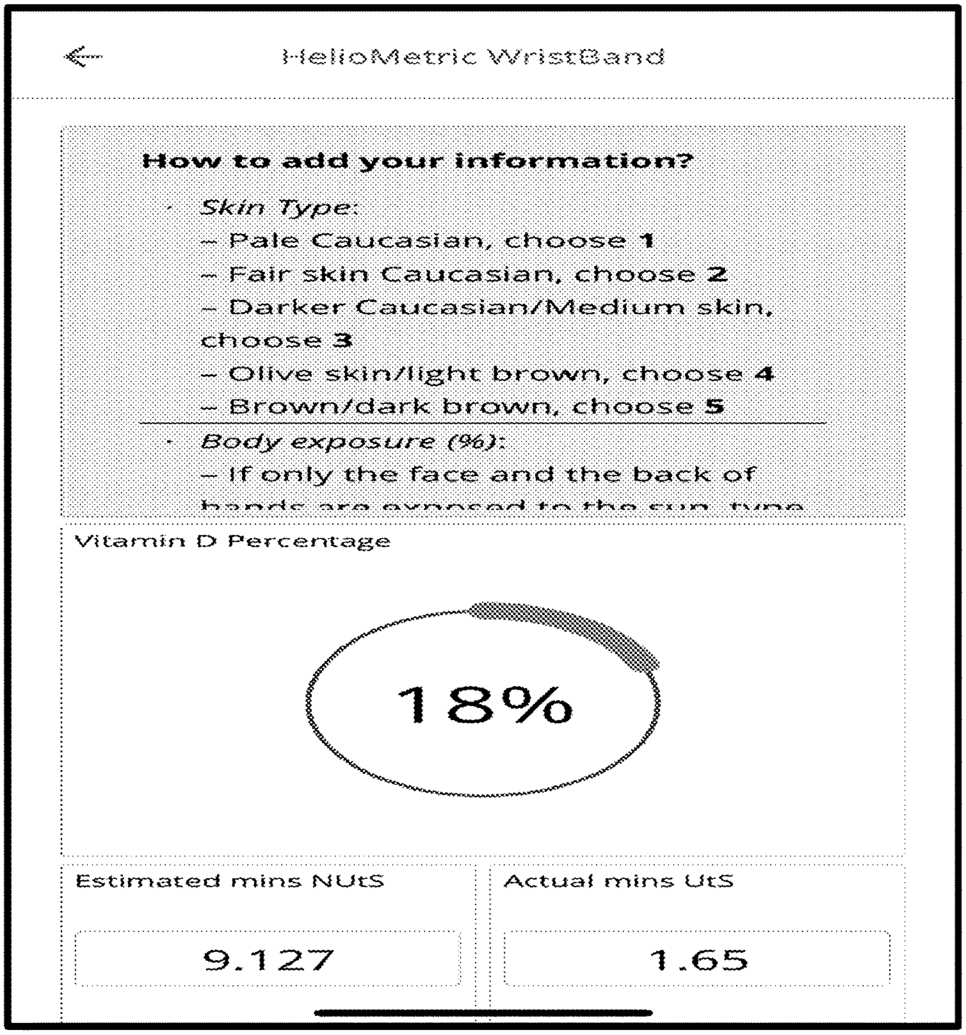
Figure 8:
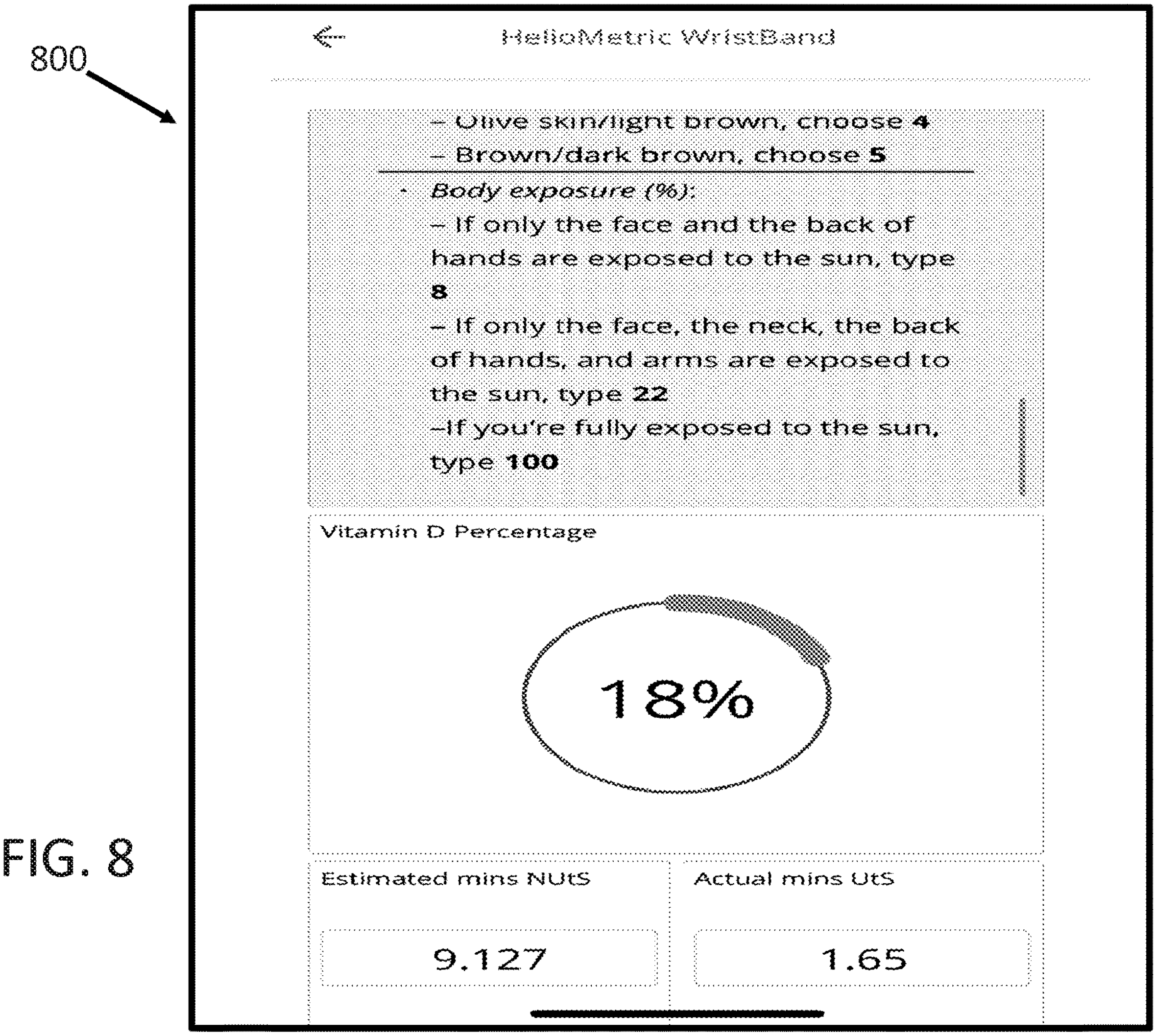

FIGS. 4, 5, and 6 describe electronic screenshots 400, 500, and 600, respectively. In embodiments, electronic screenshots 400, 500, and 600 provide disclaimer information to the user. FIGS. 7 and 8 describe electronic screenshots 700 and 800, respectively. As shown in FIGS. 7 and 8, instructions on what input into a monitoring application (such as monitoring application 1408 described in FIG. 14) are required for skin type and for body exposure.

Figure 9:
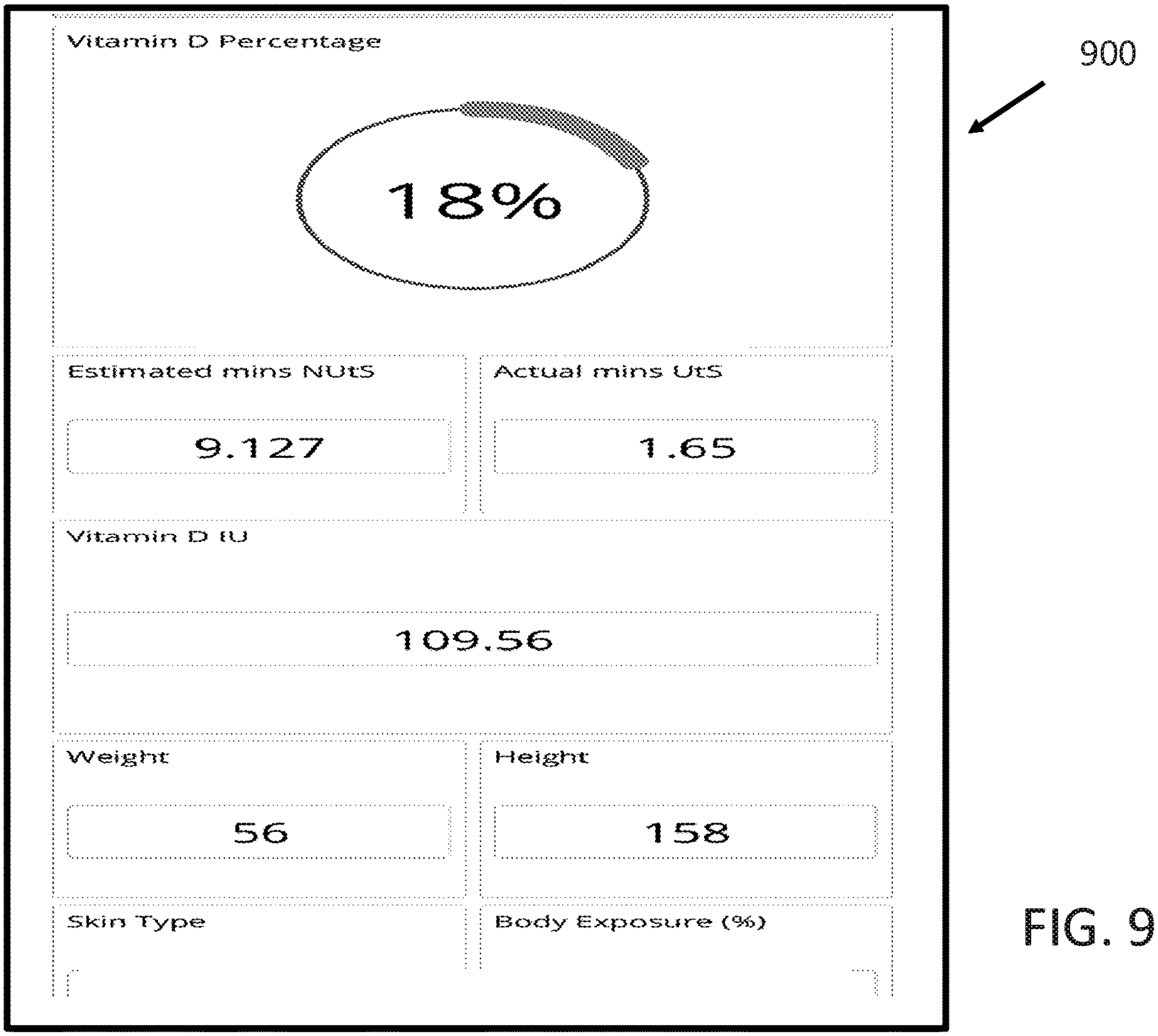
Figure 10:
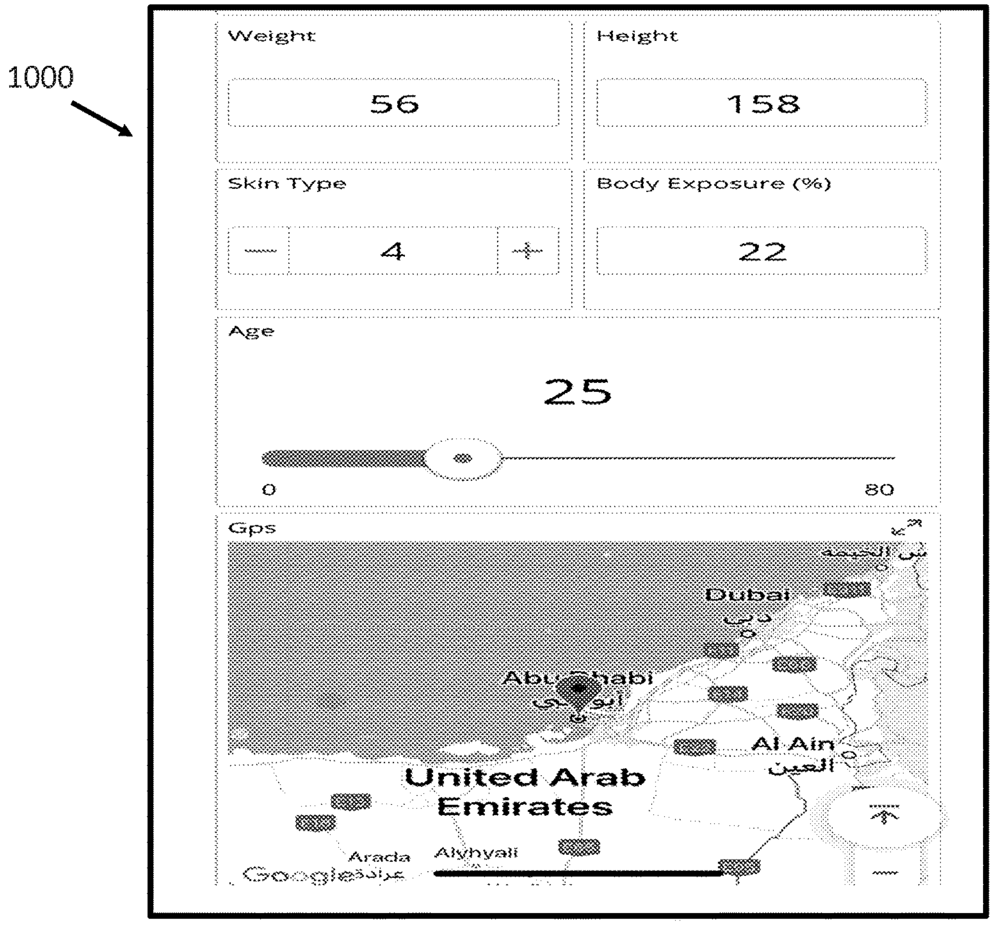
Figure 11:
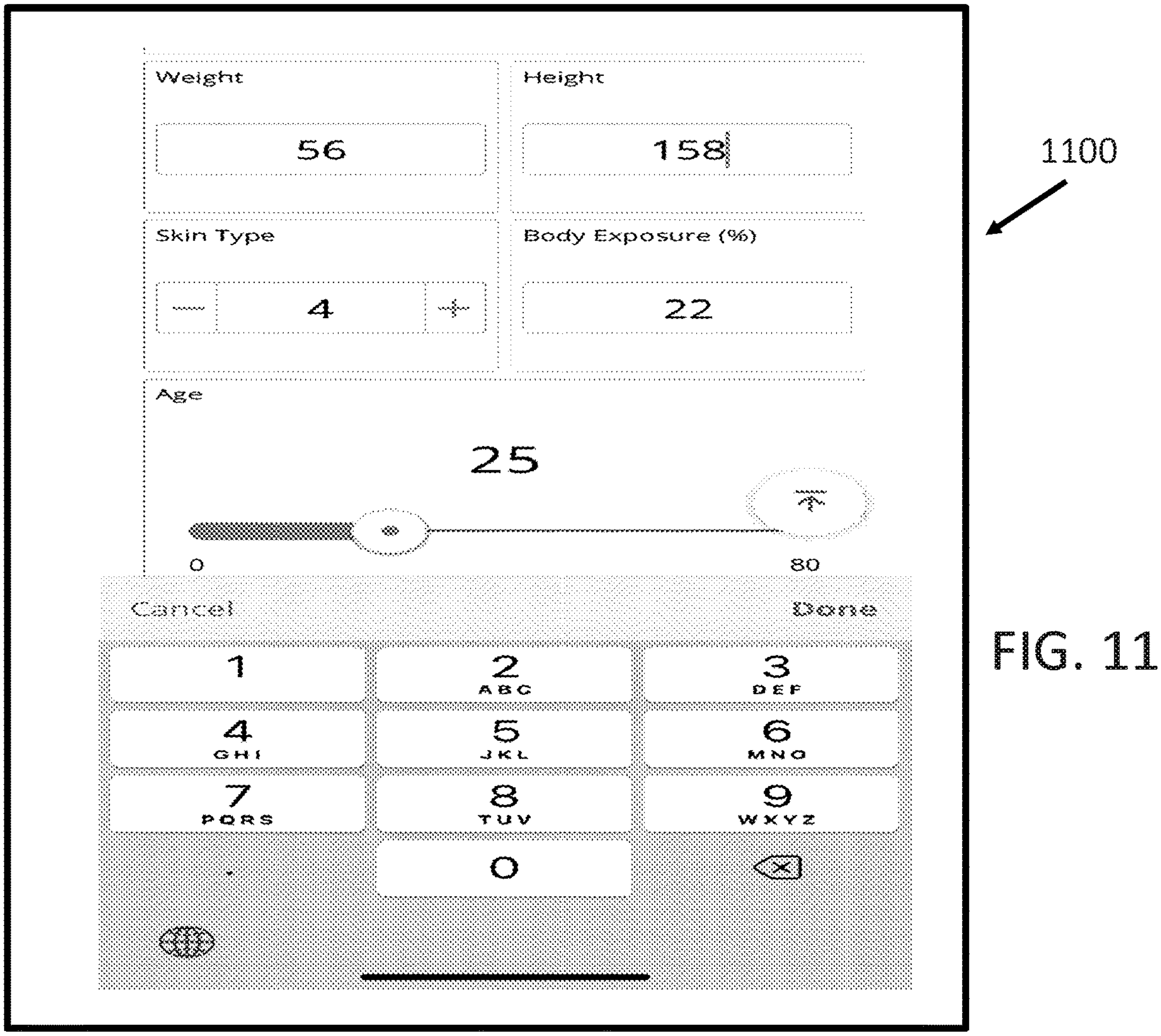
Figure 12:
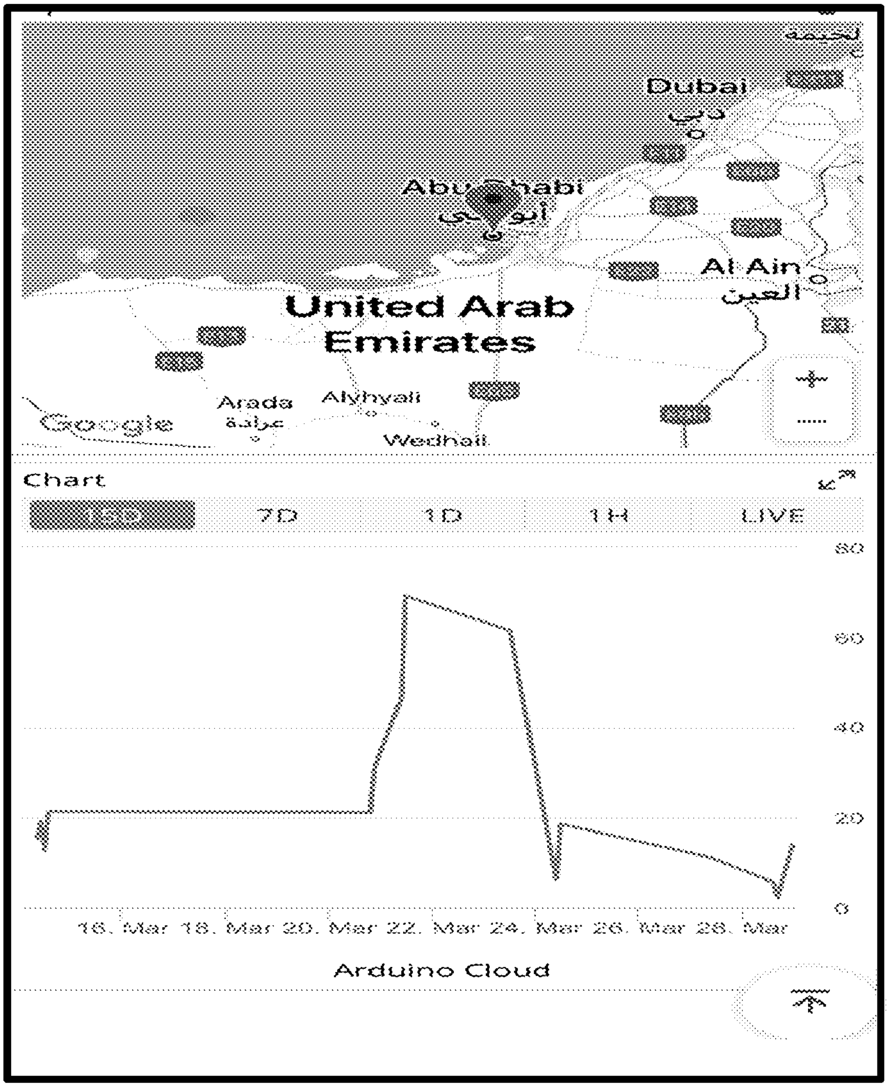

FIG. 9 describes electronic screenshot 900. In embodiments, electronic screenshot 900 shows an estimated minutes needed under the sun (NUtS) and actual minutes under the sun (UtS). Also shown in electronic screenshot 900, the amount of vitamin D IU received during a period of time is shown. FIGS. 10 and 11 describe example screenshots 1000 and 1100, respectively. Each electronic screenshot in FIGS. 10 and 11 describe examples of how age or other information can be inputted into the monitoring application. As shown in FIG. 10, age can be entered by moving a slidable button. In FIG. 11, height can be entered by using a touchscreen numerical pad area. FIG. 12 describes electronic screenshot 1200. As shown in FIG. 12, the amount of vitamin D dosage percentage (based on mins spent under the sun) is shown graphically in electronic screenshot 1200.

Figure 13:
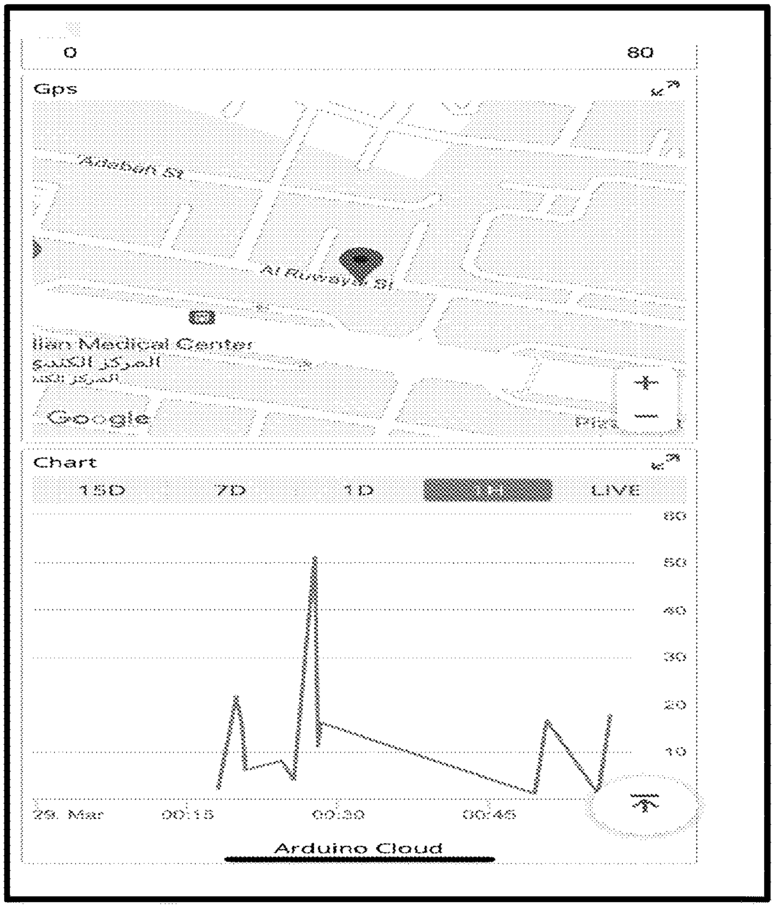

As shown in FIG. 12, the vitamin D dosage is shown over days. FIG. 13 describes electronic screenshot 1300. As shown in FIG. 13, the amount of vitamin D dosage also shown graphically; however, this time, the vitamin D dosage is shown over increments of minutes. Both electronic screenshots 1200 and 1300 include a map feature that shows the location of the user of the heliometric device. In embodiments, electronic screenshots 1200 and 1300 may be displayed via a monitoring application (e.g. monitoring application 1408).

Figure 14:
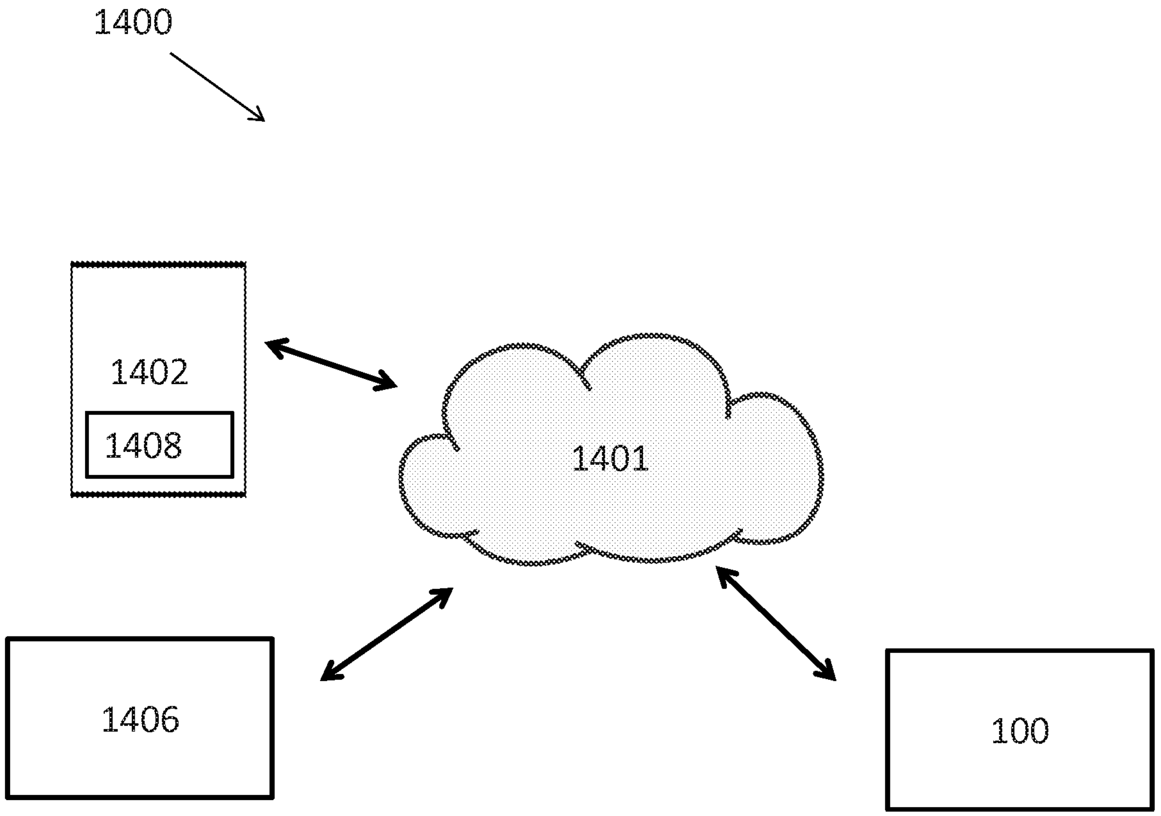
FIG. 14 is a networking environment.

FIG. 14 is a diagram of example environment 1400 in which systems, devices, and/or methods described herein may be implemented. FIG. 14 shows network 1401, user device 1402, database 1406, monitoring application 1408, and heliometric device 100.

Network 1401 may include a local area network (LAN), wide area network (WAN), a metropolitan network (MAN), a telephone network (e.g., the Public Switched Telephone Network (PSTN)), a Wireless Local Area Networking (WLAN), a WiFi, a hotspot, a Light fidelity (LiFi), a Worldwide Interoperability for Microware Access (WiMax), an ad hoc network, an intranet, the Internet, a satellite network, a GPS network, a fiber optic-based network, and/or combination of these or other types of networks. Additionally, or alternatively, network 1401 may include a cellular network, a public land mobile network (PLMN), a second generation (2G) network, a third generation (3G) network, a fourth generation (4G) network, a fifth generation (5G) network, and/or another network.

In embodiments, network 1401 may allow for devices describe any of the described figures to electronically communicate (e.g., using emails, electronic signals, URL links, web links, electronic bits, fiber optic signals, wireless signals, wired signals, etc.) with each other so as to send and receive various types of electronic communications.

User device 1402 may include any computation or communications device that is capable of communicating with a network (e.g., network 1401). For example, user device 1402 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a smart phone, a desktop computer, a laptop computer, a tablet computer, a camera, a personal gaming system, a television, a set top box, a digital video recorder (DVR), a digital audio recorder (DUR), a digital watch, a digital glass, or another type of computation or communications device.

User device 1402 may receive and/or display content. The content may include objects, data, images, audio, video, text, files, and/or links to files accessible via one or more networks. Content may include a media stream, which may refer to a stream of content that includes video content (e.g., a video stream), audio content (e.g., an audio stream), and/or textual content (e.g., a textual stream). In embodiments, an electronic application may use an electronic graphical user interface to display content and/or information via user device 1402. User device 1402 may have a touch screen and/or a keyboard that allows a user to electronically interact with an electronic application. In embodiments, a user may swipe, press, or touch user device 1402 in such a manner that one or more electronic actions will be initiated by user device 1402 via an electronic application. User device 1402 may receive electronic information from heliometric device 100 (directly or via database 1406) and generate and display graphs such as those described in the figures above. In embodiments, heliometric device may utilize computation or communication device that is capable of communicating with a network (e.g., network 1401). In embodiments, heliometric device 100 may be similar to the heliometric device described above in FIGS. 1 to 13.

User device 1402 may include a variety of applications, such as, for example, an e-mail application, a telephone application, a camera application, a video application, a multi-media application, a music player application, a visual voice mail application, a contacts application, a data organizer application, a calendar application, an instant messaging application, a texting application, a web browsing application, a blogging application, and/or other types of applications (e.g., a word processing application, a spreadsheet application, etc.). In embodiments, user device 1402 may be used to generate graphical displays (such as those described in FIGS. 3 to 13) to show various electronic outputs of heliometric device 100. While FIG. 14 shows a single user device 1402, there may be multiple user devices 1402 being used. Also, while FIG. 14 shows a single heliometric device 100, there may be multiple heliometric devices 100 being used.

Database 1406 may be a computation or communications device that is capable of communicating with a network (e.g., network 1401). In embodiments, database 1406 may store electronic information received from heliometric device 100 and/or user device 1402 (via monitoring application 1408). In embodiments, database 1406 may send electronic information either received from heliometric device 100 or user device 1402. In embodiments, database 1406 may also be stored on a cloud computing network.

Monitoring application 1408 may be an electronic application that can be downloaded onto user device 1402. In embodiments, monitoring application 1408 can display electronic information (via user device 1402), including images, maps, numbers, words, etc. In embodiments, monitoring application 1408 can also provide audio and video content that can be displayed via user device 1402.

Figure 15:
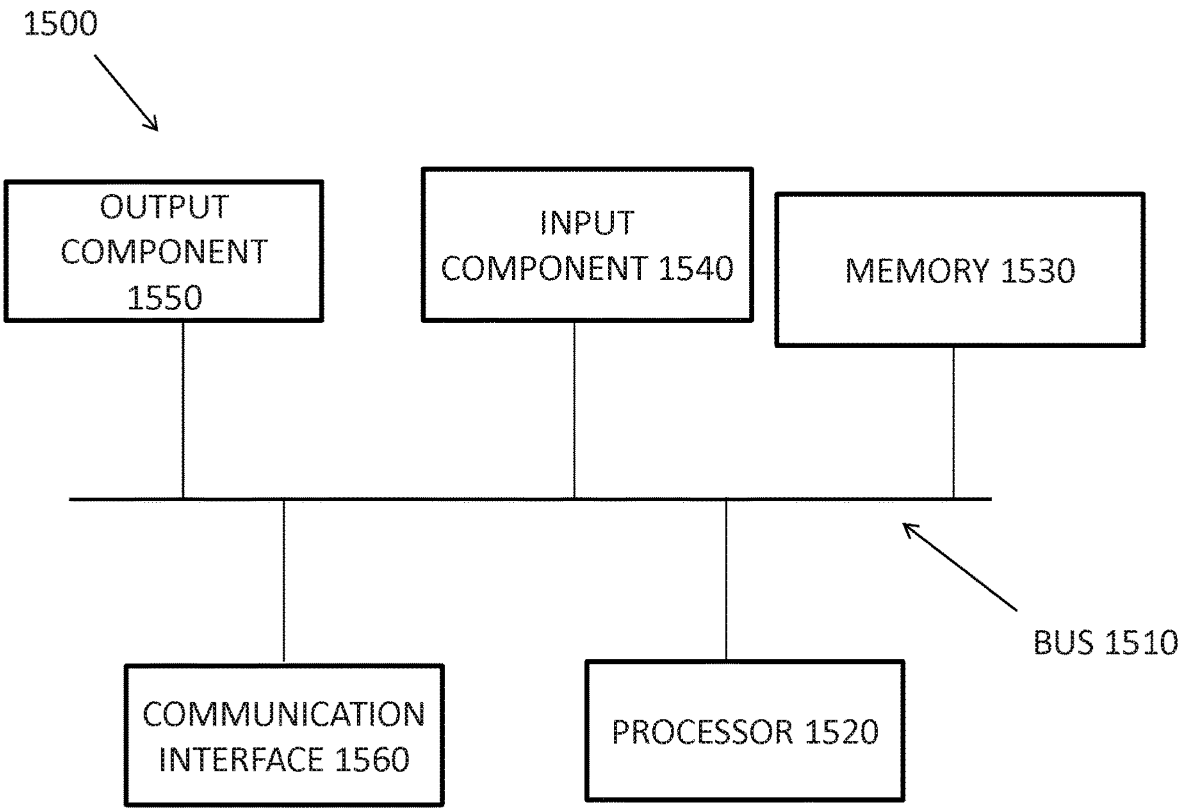
FIG. 15 is a diagram of a computer.

FIG. 15 is a diagram of example components of a device 1500. Device 1500 may correspond to user device 1402, heliometric device 100, or database 1406. Alternatively, or additionally, user device 1402, heliometric device 100, and database 1406 may include one or more devices 1500 and/or one or more components of device 1500.

As shown in FIG. 15, device 1500 may include a bus 1510, a processor 1520, a memory 1530, an input component 1540, an output component 1550, and a communications interface 1560. In other implementations, device 1500 may contain fewer components, additional components, different components, or differently arranged components than depicted in FIG. 15. Additionally, or alternatively, one or more components of device 1500 may perform one or more tasks described as being performed by one or more other components of device 1500.

Bus 1510 may include a path that permits communications among the components of device 1500. Processor 1520 may include one or more processors, microprocessors, or processing logic (e.g., a field programmable gate array (FPGA) or an application specific integrated circuit (ASIC)) that interprets and executes instructions. Memory 1530 may include any type of dynamic storage device that stores information and instructions, for execution by processor 1520, and/or any type of non-volatile storage device that stores information for use by processor 1520. Input component 1540 may include a mechanism that permits a user to input information to device 1500, such as a keyboard, a keypad, a button, a switch, voice command, etc. Output component 1550 may include a mechanism that outputs information to the user, such as a display, a speaker, one or more light emitting diodes (LEDs), etc.

Communications interface 1560 may include any transceiver-like mechanism that enables device 1500 to communicate with other devices and/or systems. For example, communications interface 1560 may include an Ethernet interface, an optical interface, a coaxial interface, a wireless interface, or the like.

In another implementation, communications interface 1560 may include, for example, a transmitter that may convert baseband signals from processor 1520 to radio frequency (RF) signals and/or a receiver that may convert RF signals to baseband signals. Alternatively, communications interface 1560 may include a transceiver to perform functions of both a transmitter and a receiver of wireless communications (e.g., radio frequency, infrared, visual optics, etc.), wired communications (e.g., conductive wire, twisted pair cable, coaxial cable, transmission line, fiber optic cable, waveguide, etc.), or a combination of wireless and wired communications.

Communications interface 1560 may connect to an antenna assembly (not shown in FIG. 15) for transmission and/or reception of the RF signals. The antenna assembly may include one or more antennas to transmit and/or receive RF signals over the air. The antenna assembly may, for example, receive RF signals from communications interface 1560 and transmit the RF signals over the air, and receive RF signals over the air and provide the RF signals to communications interface 1560. In one implementation, for example, communications interface 1560 may communicate with network 1401.

As will be described in detail below, device 1500 may perform certain operations. Device 1500 may perform these operations in response to processor 1520 executing software instructions (e.g., computer program(s)) contained in a computer-readable medium, such as memory 1530, a secondary storage device (e.g., hard disk, CD-ROM, etc.), or other forms of RAM or ROM. A computer-readable medium may be defined as a non-transitory memory device. A memory device may include space within a single physical memory device or spread across multiple physical memory devices. The software instructions may be read into memory 1530 from another computer-readable medium or from another device. The software instructions contained in memory 1530 may cause processor 1520 to perform processes described herein. Alternatively, hardwired circuitry may be used in place of or in combination with software instructions to implement processes described herein. Thus, implementations described herein are not limited to any specific combination of hardware circuitry and software.

It will be apparent that example aspects, as described above, may be implemented in many different forms of software, firmware, and hardware in the implementations illustrated in the figures. The actual software code or specialized control hardware used to implement these aspects should not be construed as limiting. Thus, the operation and behavior of the aspects were described without reference to the specific software code—it being understood that software and control hardware could be designed to implement the aspects based on the description herein.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

While various actions are described as selecting, displaying, transferring, sending, receiving, generating, notifying, and storing, it will be understood that these example actions are occurring within an electronic computing and/or electronic networking environment and may require one or more computing devices, as described in FIGS. 14 and 15 to complete such actions.

No element, act, or instruction used in the present application should be construed as critical or essential unless explicitly described as such. Also, as used herein, the article "a" is intended to include one or more items and may be used interchangeably with "one or more." Where only one item is intended, the term "one" or similar language is used. Further, the phrase "based on" is intended to mean "based, at least in part, on" unless explicitly stated otherwise.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. A method, comprising:

receiving, by a computing device, vitamin D electronic information, wherein the computing device has a light sensor, an ultraviolet sensor, and a display screen;

determining, by the computing device, a LUX level based on the light sensor, wherein the LUX level is determined by the light sensor and wherein the light sensor determines the LUX level every four seconds;

determining, by the computing device, that the LUX level is greater than 650;

determining, by the computing device, based on the LUX level being greater than 650, a particular amount of International Units (IU) needed for a particular amount of vitamin D dosage, wherein the determining the particular amount of IU needed for the particular amount of vitamin D dosage is UV index*skin type factor*body exposure*age factor*1000, wherein the UV index is determined by the ultraviolet sensor, wherein the body exposure is given a value of 100% if the person's entire body is exposed to sunlight, a value of 22% if the person's face, neck, back of hands, and arms are exposed to the sunlight, wherein the determining the particular amount of IU needed for the particular amount of vitamin D dosage is conducted in real-time; and sending, by the computing device, the particular amount of IU needed for the particular amount of vitamin D dosage to a display screen.

2. The method of claim 1, wherein the body exposure is based on the amount of the body exposed to the sun.

3. The method of claim 1, wherein the age factor value decreases with the age of a user using the computing device.

4. The method of claim 1, further comprising:

receiving, by the computing device, electronic body mass index (BMI) information;

determining, by the computing device, whether the electronic BMI information is above 30;

recalculating, by the computing device, the particular amount of IU needed for the particular amount of vitamin D dosage to include a 0.7 value based on the electronic BMI information being greater than 30.

5. The method of claim 1, wherein the determining the LUX level is based on:

the computing device determining electronic timestamp information based on how much of a period of time it takes the light sensor to measure the LUX level, continuously storing, by the computing device, electronic timestamp information wherein each stored electronic timestamp information is associated with an illuminance amount, wherein:

each electronic timestamp information is generated by the computing device based on an amount of time a person is in sunlight, each electronic timestamp information is measured in milliseconds, and a particular electronic timestamp information is added to a total time that the person is in the sunlight if the particular electronic timestamp is greater than a particular threshold and the illuminance amount is greater than another particular threshold.

6. A device, comprising:

a light sensor, an ultraviolet sensor, a strap configured to be mounted around an arm, a display screen, a memory, and a processor, coupled to the memory, to:

receive vitamin D electronic information;

determine a LUX level based on the light sensor, wherein the LUX level is determined by the light sensor and wherein the light sensor determines the LUX level every four seconds;

determine that the LUX level is greater than 650;

determine a particular amount of International Units (IU), based on the LUX level being greater than 650, needed for a particular amount of vitamin D dosage, wherein the determining the particular amount of IU needed for the particular amount of vitamin D dosage is UV index*skin type factor*body exposure*age factor*1000, wherein the determining the particular amount of IU needed for the particular amount of vitamin D dosage is conducted in real-time; and send the particular amount of IU needed for the particular amount of vitamin D dosage to a display screen.

7. The device of claim 6, wherein the device is further to:

receive electronic body mass index (BMI) information;

determine whether the electronic BMI information is above 30;

Recalculate the particular amount of IU needed for the particular amount of vitamin D dosage to include a 0.7 value based on the electronic BMI information being greater than 30.

8. The device of claim 6, wherein:

the light sensor and the ultraviolet sensor are located within a shield device that is part of the device, and the shield device is mounted onto a microelectronic circuit board of the device.

9. The device of claim 6, wherein the determining the LUX level is based on:

the computing device determining electronic timestamp information based on how much time it takes the light sensor to measure the LUX level, continuously storing, by the computing device, electronic timestamp information wherein each stored electronic timestamp information is associated with an illuminance amount, wherein:

each electronic timestamp information is generated by the computing device based on an amount of time a person is in sunlight, each electronic timestamp information is measured in milliseconds, and a particular electronic timestamp information is added to a total time that the person is in the sunlight if the particular electronic timestamp is greater than a particular threshold and the illuminance amount is greater than another particular threshold.

10. The device of claim 9, wherein the processor is further to:

determine that the LUX level is below 650;

determine an additional timestamp for a period of time that the LUX level is below 650; and subtract the period of time that the LUX level is below 650 from the total time that the person is in the sunlight.

* * * * *